(12) United States Patent
Greenfield et al.

(10) Patent No.: US 7,932,021 B2
(45) Date of Patent: Apr. 26, 2011

(54) LUPUS ANTICOAGULANT TESTING

(75) Inventors: Robert Greenfield, Trumbull, CT (US); Enriqueta Guinto, Greenwich, CT (US)

(73) Assignee: American Diagnostica, Inc., Stamford, CT (US)

( * ) Notice: Subject to any disclaimer, the term of this patent is extended or adjusted under 35 U.S.C. 154(b) by 415 days.

(21) Appl. No.: 11/191,891

(22) Filed: Jul. 28, 2005

(65) Prior Publication Data

US 2007/0026467 A1 Feb. 1, 2007

(51) Int. Cl.
*G01N 33/53* (2006.01)
(52) U.S. Cl. ............................. 435/2; 436/8; 436/174
(58) Field of Classification Search ............... 435/6, 13, 435/69.9; 436/8
See application file for complete search history.

(56) References Cited

U.S. PATENT DOCUMENTS

| | | | |
|---|---|---|---|
| 4,877,741 A * | 10/1989 | Babcock et al. | 436/8 |
| 5,766,869 A | 6/1998 | Arkel et al. | |
| 5,922,551 A * | 7/1999 | Durbin et al. | 435/7.21 |
| 6,100,072 A * | 8/2000 | Brucato et al. | 435/69.7 |
| 2003/0064414 A1 | 4/2003 | Benecky et al. | |
| 2003/0104493 A1 | 6/2003 | Ortel et al. | |
| 2005/0175983 A1* | 8/2005 | Okuda | 435/4 |
| 2005/0221414 A1 | 10/2005 | Varadi et al. | |

FOREIGN PATENT DOCUMENTS

EP 0566333 * 4/1993

OTHER PUBLICATIONS

Rosove et al. (Blood 1986, vol. 68, p. 472-478).*
Notification of Transmittal of International Search Report, Feb. 28, 2006.
Sigurd Liestol, et al., Dilute Prothrombin Time-Based Lupus Ratio Test Integrated LA Testing With Recombinant Tissue Thromboplastin, Thrombosis Research (2002) vol. 105, p. 177-182.
R. Schjetlein, et al., A Quantitative, Semi-Automated And Computer-Assisted Test Fro Lupus Anticoagulant, Thrombosis Research (1993) vol. 69, p. 239-250.
Rune Schjetlein, et al, An Evaluation of Two Commercial Test Procedures For The Detection Of Lupus Anticoagulant, American Journal of Clinical Pathology (1995) vol. 103, No. 1, p. 108-111.
Extended European Search Report (EP 05 776 736.0), 2006.
Mackie, J. I., et al., (2000) Antiphospholipid Syndrome, London, UK: Springer; pp. 214-224.
Loizou, S., et al., (1985) Clin. Exp. Immunol. 62: 739-744.
McNeil, H. P. et al., (1990) Proc. Natl. Acad. Sci. USA 87: 4120-4124.
Galli, M. et al., (1990) Lancet 334: 1544-1547.
Arvieux, J. et al., (1995) Thromb. Haemost. 74: 1120-1125.
Galli, M. et al., (1992) Thromb. Haemost. 68: 297-300.
Galli, M. et al., (1997) Thromb. Haemost.77: 486-491.
Asherson, R. A., et al.(1989) Medicine 68: 366-374.
Alarcon-Segovia, D. et al., (1989) Medicine 68: 353-365.
Conley and Hartmann ((1952) J. Clin. Invest. 31: 621-622.
Thiagarajan, P. et al., (1980) J. Clin. Invest. 66: 397-405.
Triplett, D. A. (2002) Arch. Pathol. Lab. Med. 126(11): 1424-1429.
Thiagarajan, P. et al., (1986) Blood 68: 869-874.
Exner, T. et al., (1990) Blood Coag. Fibrinol. 1: 259-266.
Triplett, D. A. et al., (1983) Am. J. Clin. Path. 79: 678-682.
Arnout, J.et al., (1994) Br. J. Haematol. 87: 94-9.
Mackie, J.I. et al., (2004) Thromb. Res. 114: 673-674.
Liestol, S. et al, (1983) Thromb. Res. 105: 177-182.

\* cited by examiner

*Primary Examiner* — Jacob Cheu
(74) *Attorney, Agent, or Firm* — Frommer Lawrence & Haug LLP

(57) ABSTRACT

The present invention relates generally to the field of diagnostic screening and diagnostic assays. In particular, the present invention provides an improved, rapid, and efficient method of screening for antiphospholipid antibodies, such as lupus anticoagulants (LA). The invention also relates to a kit for screening plasma levels for antiphospholipid antibodies in subjects in need thereof, such as those at risk for or suffering from, inter alia, antiphospholipid syndrome (APS) and systemic lupus erythromatosus (SLE).

10 Claims, No Drawings

LUPUS ANTICOAGULANT TESTING

FIELD OF THE INVENTION

The present invention relates generally to the field of diagnostic screening and diagnostic assays. In particular, the present invention relates to an improved, rapid, and efficient method of screening for antiphospholipid antibodies, such as lupus anticoagulants (LA). The invention also relates to a kit for screening plasma levels for antiphospholipid antibodies in subjects in need thereof, such as those at risk for or suffering from, inter alia, antiphospholipid syndrome (APS) and systemic lupus erythromatosus (SLE). Other aspects of the invention are obvious from, or are within the ambit of the invention.

BACKGROUND OF THE INVENTION

Antiphospholipid antibodies are a heterogeneous family of immunoglobulins that includes, among others, lupus anticoagulants and anticardiolipin antibodies. Lupus anticoagulants (LA) behave as acquired inhibitors of coagulation, prolonging phospholipid-dependent in vitro coagulation assays (Mackie, J. I., et al., (2000) Antiphospholipid Syndrome, London, UK: Springer; pp. 214-224), whereas anticardiolipin antibodies are measured by immunoassay, utilizing cardiolipin or other anionic phospholipids in solid phase (Loizou, S., et al., (1985) Clin. Exp. Immunol. 62: 739-744). Despite their name, antiphospholipid antibodies do not recognize phospholipids, but instead recognize plasma proteins bound to suitable anionic, but not necessarily phospholipid, surfaces. Among these, β2-glycoprotein 1 (McNeil, H. P. et al., (1990) Proc. Natl. Acad. Sci. USA 87: 4120-4124; Galli, M. et al., (1990) Lancet 334: 1544-1547) and prothrombin (Arvieux, J. et al., (1995) Thromb. Haemost. 74: 1120-1125) are the most commonly investigated antigenic targets. Most anticardiolipin antibodies require β2-glycoprotein 1 (β2-GP1) to react with cardiolipin in immunoassays (Galli, M. et al., (1990) Lancet 334: 1544-1547).

Specific subgroups of anti-β2-GP1 (Galli, M. et al., (1992) Thromb. Haemost. 68: 297-300) and antiprothrombin antibodies (Galli, M. et al., (1997) Thromb. Haemost. 77: 486-491) are responsible for the lupus anticoagulant activity in phospholipid-dependent coagulation tests. Two forms of antiphospholipid syndrome (APS) have been described: a "primary" syndrome (Asherson, R. A., et al., (1989) Medicine 68: 366-374), with no evidence of an underlying disease, and a "secondary" syndrome (Alarcon-Segovia, D. et al., (1989) Medicine 68: 353-365), mainly in the context of systemic lupus erythematosus (SLE). Thromboembolytic events are reported in approximately one-third of antiphospholipid-positive subjects. However, the results of clinical studies are largely influenced by factors such as differences in study design and eligibility criteria, and by the diversity of antiphospholipid antibodies in terms of types, isotypes, cut-off, and laboratory methods employed for their detection.

Primary APS is a pathological hemostatic condition characterized by unexplained thrombosis, recurrent fetal loss, thrombocytopenia, and/or neurological disorders. Secondary APS occurs when antiphospholipid antibodies are present in subjects with other autoimmune disorders such as SLE, as originally described by Conley and Hartmann ((1952) J. Clin. Invest. 31: 621-622). The development of antiphospholipid antibodies may also result from the administration of drugs such as chlorpromazine, procainamide, thorazine and other medications. LA autoantibodies are directed against heterogeneous complexes of anionic phospholipids (e.g. cardiolipin, phosphatidylinositol, phosphatidylethanolamine and phosphatidylserine) (Thiagarajan, P. et al., (1980) J. Clin. Invest. 66: 397-405) and phospholipid-binding proteins (Triplett, D. A. (2002) Arch. Pathol. Lab. Med. 126(11): 1424-1429) in plasma. The major protein components of the LA autoantigens include β2-GPI, prothrombin and annexin V. LA antiphospholipid antibodies are characterized by their ability to prolong in vitro clotting times in coagulation-based assays such as phospholipid-sensitive aPTT (active partial thromboplastin time), kaolin clotting time, dilute Russell's Viper Venom Time test (e.g. DVVtest®, American Diagnostica Inc.) and dilute prothrombin time (dPT) tests (Thiagarajan, P. et al., (1986) Blood 68: 869-874; Exner, T. et al., (1990) Blood Coag. Fibrinol. 1: 259-266).

The aPTT assay is a kinetic assay that measures the recalcification time of plasma. By activating the plasma to a maximum level before clotting can occur, aPTT is used to screen subjects with a bleeding tendency for deficiencies in coagulation factors involved in the intrinsic pathway (Factor VII and Factor XIII excluded) and to determine the presence of a non-specific inhibitor, such as an LA. The aPTT assay is also used to evaluate the effect of therapy and to monitor and regulate heparin therapy. In this assay, kaolin (powdered silica, Celite or ellagic acid) is added to the plasma for approximately 3 minutes, depending on the activator, at 37° C. to activate it, after which partial thromboplastin (cephalin or soya phosphatide) and calcium chloride are added to induce clotting. Prolongation of aPTT can be caused by a deficiency in one of the clotting factors involved in the intrinsic pathway, especially Factors XII, XI, X, IX, VIII, V, II and I. Prolonged aPTT is seen after a massive blood transfusion, heparin therapy, hemophilia A, acquired Factor VIII inhibitor, antiphospholipid antibodies, over-anticoagulation with coumarins, heparin therapy, or an error in specimen collection. When a prolonged aPTT is observed, more specific single factor assays and mixing studies are performed to identify its exact cause.

Clinical studies show that a dPT is an effective antiphospholipid coagulation assay and can identify antiphospholipid antibodies that are not detected in other assays (e.g. phospholipid-sensitive aPTT and dRVVT)(Liestol, S. et al., (2002) Thromb. Res. 105: 177-82; Triplett, D. A. et al., (1983) Am. J. Clin. Path. 79: 678-682; Arnout, J. et al., (1994) Br. J. Haematol. 87: 94-9). The addition of a dPT assay to the antiphospholipid antibody testing panel has been shown to increase the sensitivity of detecting LA in subject samples (Mackie, J. I. et al., (2004) Thromb. Res. 114: 673-674).

ACTICLOT® dPT™ (American Diagnostica Inc.) is an example of a fully integrated dilute prothrombin time diagnostic kit for screening and confirming the presence of phospholipid-dependent LA autoantibodies for the definitive diagnosis APS. The ACTICLOT® dPT™ activator used for the screening protocol contains a unique formulation of lipidated recombinant tissue factor and calcium. The ACTICLOT® LA Phospholipid reagent used in the confirmatory protocol contains a unique formulation of phospholipids specifically designed to demonstrate the phospholipid-dependent nature of the LA's detected in samples that are positive in the ACTICLOT® dPT™ screening protocol.

A commonly used protocol is the combined DVVtest® and DVVconfirm® assay (American Diagnostica). DVVtest® is a dilute Russell's Viper Venom Time (dRVVT) assay intended for the determination of LAs in subject plasma. DVVconfimm®is intended to confirm the presence of LAs in plasma that tested positive using the DVVtest®. All DVV test reagents normally used for screening contain Russell's viper venom (RVV) as the active component. DVV test reagents containing RVV directly activate Factor X to Factor Xa in the presence of a low level of phospholipids and calcium, converting fibrinogen to fibrin and leading to detectable clot formation in plasma. This direct activation bypasses the Contact and Intrinsic Factors in the coagulation cascade, thereby excluding interference from deficiencies of Factors VIII, IX, XI, and XII, or their respective inhibitors.

DVV confirmatory reagents contain Russell's viper venom and a high amount of several phospholipids. The screening of plasma involves mixing DVV test reagents with subject plasma and determining the clotting time. A prolonged clotting time relative to normal plasma is indicative of the presence of LA. If the plasma contains LA, the plasma is then retested with the DVV confirmatory reagent and should have a significantly reduced clotting time relative to that with DVV test reagent. The reduced clotting time with DVV confirmatory reagents is due to high phospholipids in the DVV confirmatory reagent that neutralize the LA autoantibodies.

One problem with this approach is that coagulation-based test and confirmatory reagents must be matched to one another to obtain a positive result. This is because both reagents contain phospholipids and a procoagulant activator reagent, which initiate clot formation. If the test reagent and confirmatory reagent are not matched correctly, then false positives or false negatives can be obtained. This also makes manufacturing more difficult. During manufacturing of the reagents, the activity of the active components may change, which makes it difficult to properly match the two test and confirmatory reagents.

Due to the heterogeneous nature of the pathological phospholipid-dependent autoantibodies, it is widely recognized that no single LA coagulation assay identifies all LA antibodies. In 1995, the International Society on Thrombosis and Haemostatis (ISTH) Scientific Subcommittee on Antiphospholipid Antibodies recommended that each plasma sample suspected of containing LA should be tested in at least two LA diagnostic assays to increase the probability of identifying LA (Liestol, S. et al, (1983) Thromb. Res. 105: 177-182). Additionally, the ISTH SSC recommended that a definitive diagnosis of LA also require demonstration of the phospholipid-dependent nature of the autoantibodies. This is accomplished by performing a second confirmatory coagulation assay in the presence of high amounts of phospholipids. The hallmark of the presence of LA is a significant reduction of clotting time of the high phospholipid confirmatory assay as compared to the low phospholipid-screening assay.

Using the same active reagents in both the testing/screening and confirmatory steps of a coagulation-based LA assay, therefore, would be a significant advance in the art to prevent the problems of these testing protocols. Furthermore, a common reagent useful in all three LA coagulation-based assays would significantly decrease the time and labor involved in diagnosing and/or monitoring disorders characterized by the presence of antiphospholipid antibodies.

SUMMARY OF THE INVENTION

As discussed above, current recommendations by the ISTH Subcommittee include performance of multiple screening tests to ensure that antiphospholipid antibodies such as LAs are not missed or inadvertently overlooked. Additionally, a positive antiphospholipid screening assay requires separate confirmation with a substrate comprising high levels of phospholipids. Both the initial screening assay and the confirmatory assay must each utilize separate test and confirmatory reagents that have extremely similar, if not identical, activities, greatly increasing the likelihood of false positives and/or false negatives.

With the purpose of streamlining antiphospholipid antibody testing and diagnosis, it has now been surprisingly demonstrated that existing diagnostic assays for antiphospholipid antibodies such as Las (dRVVT) assay, the aPTT assay, and the dPT assay, can be performed with one high phospholipid substrate. It is now possible to easily match the results obtained from an antiphospholipid-screening test to the confirmatory test, which is very difficult using currently available assays and methods. A particular advantage of the present invention is that any plasma sample testing positive in dRVVT, DVV, aPTT, or dPT screening assays can be subsequently confirmed with the one phospholipid substrate, thereby increasing the efficiency of diagnosis and detection of antiphospholipids such as LAs.

Accordingly, in one aspect of the invention, an assay kit for detecting antiphospholipid antibodies in a test plasma sample is provided, comprising at least one control plasma sample, at least one procoagulant test reagent, and a high phospholipid substrate, wherein the kit comprises a DVV, an aPTT, and an dPT, each assay comprising a screening step and a confirmatory step, wherein the confirmatory step of each assay uses the same high phospholipid substrate.

In one embodiment, the antiphospholipid antibodies comprise lupus anticoagulants, anti-β2-GP1 antibodies, anti-protein C antibodies, anti-protein S antibodies, anti-complement antibodies, anticardiolipin antibodies, anti-thrombin antibodies, anti-prothrombin antibodies, anti-thrombomodulin antibodies, anti-tPA antibodies, anti-Factor XII antibodies, anti-kininogen antibodies, and anti-annexin V antibodies.

In another embodiment, the test plasma sample is derived from a subject at risk for or suffering from an autoimmune disorder. The autoimmune disorder can be selected from antiphospholipid syndrome (APS), connective tissue diseases, immune thrombocytopenia purpura, Hashimoto's thyroiditis, rheumatoid arthritis, and systemic lupus erythromatosus (SLE).

In yet another embodiment, the at least one control plasma sample is derived from at least one subject having low or absent levels of antiphospholipid antibodies and/or at least one subject having high levels of antiphospholipid antibodies.

Another embodiment of the present invention provides at least one procoagulant test reagent comprising Russell's viper venom, Taipan snake venom, textarin, ecarin, thrombin, kaolin, silica, ellagic acid, and tissue factor. The at least one procoagulant test reagent can further comprise a low level of phospholipids.

The high phospholipid substrate can comprise phosphatidylserine, phosphatidylcholine, phosphatidylethanolamine, phosphatidylinositol, cardiolipin, phosphatidic acid, dioleoylphosphatidylethanolamine (DOPE), phospholipid coated beads, phospholipid suspensions, and combinations thereof.

The assay kit of the present invention can also further comprise a buffer containing calcium. Preferably, the calcium concentration is about 1-25 mM.

Another aspect of the present invention provides a method of detecting antiphospholipid antibodies in a subject at risk for or suffering from an autoimmune disorder characterized by the presence of antiphospholipid antibodies and a decreased rate of coagulation. The method comprises contacting a first test plasma sample derived from the subject with a procoagulant test reagent containing a low level of phospholipids, measuring the rate of coagulation in the first test plasma sample, contacting a second test plasma sample derived from the subject with the procoagulant test reagent and a high phospholipid substrate, measuring the rate of coagulation in the second test plasma sample, and comparing the rates of coagulation from the two test samples. A decreased rate of coagulation in the second test, as compared with the first test, indicates the presence of antiphospholipid antibodies in the first and second test plasma samples. Optionally, coagulation rates of the test samples can be compared with control coagulation rates measured in samples from normal subjects.

In one embodiment, the first and second test plasma samples are the same.

In another embodiment, the detection comprises spectrophotometry.

Another aspect of the present invention provides a method of diagnosing an autoimmune disorder characterized by the presence of antiphospholipid antibodies and a decreased rate of coagulation in a subject at risk for or suffering from the autoimmune disorder. The method comprises contacting a first test plasma sample derived from the subject with a first procoagulant test reagent containing a low level of phospholipids, measuring the rate of coagulation in the first test plasma sample, contacting a second test plasma sample derived from the subject with the first procoagulant test reagent and a high phospholipid substrate, measuring the rate of coagulation in the second test plasma sample, and comparing the rates of coagulation from the first and second tests. A decreased rate of coagulation in the second test, as compared with first test, indicates the presence of antiphospholipid antibodies in the test plasma sample. Optionally, the first and second test plasma samples are tested with a second procoagulant test reagent, and the tests can be repeated using a third procoagulant test reagent.

In one embodiment, all of the test plasma samples are the same.

In another embodiment, the first, second, and third procoagulant test reagents are independently selected from the group consisting of Russell's viper venom, Taipan snake venom, textarin, ecarin, thrombin, kaolin, thromboplastin, and tissue factor.

Another aspect of the present invention provides a method of decreasing the likelihood of false positives in one or more coagulation assays used in diagnosing an autoimmune disorder characterized by the presence of antiphospholipid antibodies and a decreased rate of coagulation. In this embodiment, the coagulation assay comprises a screening step and a confirmatory step, the screening step comprising contacting a test plasma sample with a procoagulant containing a low level of phospholipids, measuring the rate of coagulation in the test plasma sample, and the confirmatory step comprising contacting the test sample with the procoagulant and a high phospholipid substrate, wherein the same procoagulant is used in the screening step and the confirmatory step, thereby decreasing the likelihood of false positives in the one or more coagulation assays.

In one embodiment, the one or more coagulation assays comprise an aPTT assay, a dPT assay, and/or a DVV assay.

In another embodiment, the test plasma sample is derived from a subject at risk for, or suffering from, an autoimmune disorder.

These and other embodiments are disclosed or are obvious from and encompassed by, the following Detailed Description.

DETAILED DESCRIPTION OF THE INVENTION

In this disclosure, "comprises," "comprising," "containing" and "having" and the like can have the meaning ascribed to them in U.S. Patent law and can mean "includes," "including," and the like; "consisting essentially of" or "consists essentially of" likewise has the meaning ascribed in U.S. Patent law and the term is open-ended, allowing for the presence of more than that which is recited, so long as basic or novel characteristics of that which is recited are not changed by the presence of more than that which is recited, but excludes prior-art embodiments.

The present invention relates to kits and methods of detecting antiphospholipid antibodies in test plasma samples derived from subjects at risk for, or suffering from, an autoimmune disorder characterized by antiphospholipid antibodies and a decreased rate of coagulation, as compared to test or control samples derived from subjects that are not at risk, or are not suffering from an autoimmune disorder. The kits and methods of the invention provide an efficient, streamlined method of diagnosing autoimmune disorders by providing reagents that can be used, both in individual coagulation assays requiring a screening and a confirmatory step, and also in multiplex assays that include one or more commonly used coagulation assays known in the art to monitor the presence of antiphospholipid antibodies, such as, for example, aPTT assays, dPT assays, and DVV assays.

A "subject" in the context of the present invention can be a vertebrate, such as a mammal, bird, reptile, amphibian or fish; more advantageously a human, or a companion or domesticated or food-producing or feed-producing or livestock or game or racing or sport or laboratory animal such as murines, primates, bovines, canines, felines, caprines, ovines, porcines, or equines, or even avians. Preferably, the subject is a human.

Hemostasis is the physiological process of maintaining blood in a fluid state within intact blood vessels and preventing excess blood loss by arresting flow via the formation of a hemostatic plug (a clot). Normal hemostasis is maintained by tightly regulated interactions of the blood vessel wall, blood platelets, and blood plasma proteins. Under normal conditions, there is a delicate balance between the individual components of the hemostatic system. Any disturbances in this hemostatic balance (hemostatic potential) could result in bleeding or thrombosis. Hemostatic potential can mean the ability to maintain a balance between procoagulant and anticoagulant states, as measured by fibrin polymerization, when a trigger or activator initiates coagulation.

The coagulation process is complex, requiring interdependence of many varied components, and can be divided into four dependent phases: (1) the initiation phase, (2) the propagation phase, (3) the amplification phase, and (4) the polymerization phase. All of the phases are affected by regulatory and feedback processes known as anticoagulant pathways.

Initiation or triggering of coagulation occurs by exposure of tissue factor, due to vascular damage, plaque rupture, or monocyte expression as a result of inflammation. Trace amounts of Factor VIIa and tissue factor form the extrinsic Xase complex. This complex enhances the catalytic activity of VIIa toward Factors X and IX, resulting in the formation of the active enzymes Xa and IXa. Factor Xa generated by the extrinsic Xase complex forms a small amount of thrombin (IIa). The thrombin generated is capable of activating small amounts of the cofactors VII and V. In vivo, the extrinsic Xase complex is quickly inactivated by Tissue Pathway Factor Inhibitor (TFPI) via the formation of a quaternary complex consisting of tissue factor, VIIa and Xa. Under physiological conditions, the extrinsic Xase generates only picomolar amounts of thrombin.

During the propagation phase of coagulation, the role of the extrinsic Xase is minimized and the complex of the enzymes IXa and its cofactor VIIIa alternatively generate Factor Xa. This enzyme complex is referred to as intrinsic Xase. Formation of the Xa by the intrinsic Xase complex is approximately 50 fold more efficient than the extrinsic Xase. Factor Xa and its activated cofactor, Factor Va, form a complex on the surface of activated platelets. This is an efficient catalyst for the conversion of prothrombin to thrombin, referred to as the prothrombinase complex. Thrombin formed via the intrinsic Xase complex is capable of amplifying its own production by positive feedback (activation). Thrombin activates Factors VII and V and Factor XI activation leads to further production of the enzymatic component of intrinsic Xase (Factor IXa). Normal thrombin production is highly regulated and localized. TFPI neutralizes the trigger for thrombin generation. Active proteases (IIa, Xa, IXa) must be inactivated by protease inhibitors, such as antithrombin III (ATIII) to avoid disseminated thrombosis. Both thrombin and Xa, and to a lesser extent IXa released from membrane surfaces, are rapidly inhibited by ATIII. Thrombin can also bind non-damaged sub-endothelium via a receptor molecule, Thrombomodulin (TM). The formation of the IIa/TM complex changes the substrate specificity of thrombin from a procoagulant to an anticoagulant. Thrombin bound to TM is a potent activator of Protein C, converting it to the active enzyme Activated Protein C (APC). APC together with its cofactor protein S cleaves activated cofactors Factor VIIa and Factor Va yielding their inactive forms, Factor VIIIi and Factor Vi. TM also accelerates the inactivation of thrombin by ATIII.

The formation of thrombin leads ultimately to cleavage of fibrinogen to form fibrin. During the polymerization phase, Factor XIIIa, an enzyme generated by thrombin activation, mediates cross-linking of soluble fibrin strands. The thrombin-TM complex activates the procarboxypeptidase thrombin activated fibrinolysis inhibitor (TAFI). Thus, thrombin plays a role during this phase by both influencing the architecture and stabilization of the fibrin clot. Thrombin is a key enzyme and effector of the coagulation process. Thrombin is both a potent procoagulant and anticoagulant. However, it is thrombin's ability to cleave fibrinogen and its contribution to fibrin polymerization events that are critical to maintaining stasis.

Clot initiation, often referred to as clotting time, occurs at the intersection between the initiation and propagation phases, when only approximately 5% of thrombin has been formed. The majority of the thrombin formed is generated after the initiation of fibrin polymerization, and thus, the rate of fibrin polymerization is a more sensitive indicator of the dynamics or rate of coagulation. Changes in the propagation phase, amplification phase and anticoagulant pathways alter the rate of thrombin generation and the impact of thrombin availability on rate of fibrin polymerization. Variations in concentration or quality of the fibrinogen or fibrin strands can only be measured as a function of the actual polymerization process. Assays currently used to assess variations in the coagulation process typically can only assess variations in one or two phases. These assays measure events independently and therefore negate or eliminate the ability to detect variations in the other phases or interactions between the various phases.

Coagulation assays are available as manual methods where clot formation can be observed in a test tube either by tilting the tube or removing fibrin strands by a wire loop. The goal is to determine if a subject's blood or plasma sample can clot after certain materials are added. The amount of time from initiation of the reaction to the point of clot formation in vitro is related to congenital disorders, acquired disorders, and therapeutic monitoring. To remove the inherent variability associated with the subjective endpoint determinations of manual techniques, instrumentation and automation have been developed and introduced to measure clot time, based on electromechanical properties, clot elasticity, light scattering, fibrin adhesion, and impedance. For light scattering methods, data is gathered that represents the transmission of light through the specimen as a function of time (an optical time-dependent measurement profile).

Three assays, the dPT, aPTT, and dRVVT (DVV) are widely used to screen for abnormalities in the coagulation system, although several other screening assays can be used, e.g. protein C, fibrinogen, protein S and/or annexin V. If screening assays show an abnormal result, one or several additional assays are needed to isolate the exact source of the abnormality. Determination of dPT, DVV, and aPTT assays can rely upon coagulation analyzers which measure the time required for clot formation, that is, a single, endpoint measurement. Some coagulation analyzers determine results of the dPT, DVV, and aPTT assays by measuring the rate of clot formation using the amplitude of the change in optical or electronic signal. This type of measurement records clot formation over time.

Blood coagulation is affected by administration of drugs, in addition to the vast array of internal factors and proteins that normally influence clot formation. For example, heparin is a widely used therapeutic drug to combat existing thrombosis or to prevent thrombosis following surgery or under other conditions. The administration of heparin is typically monitored using the aPTT assay, which gives a prolonged clot time in the presence of heparin. Clot times for dPT assays are affected to a much smaller degree. Since a number of other plasma abnormalities may also cause prolonged aPTT results, the ability to discriminate between these effectors from screening assay results may be clinically significant.

An "autoimmune disorder characterized by the presence of antiphospholipid antibodies and a decreased rate of coagulation" include, but are not necessarily limited to, antiphospholipid syndrome (APS), connective tissue diseases, immune thrombocytopenia purpura, Hashimoto's thyroiditis, rheumatoid arthritis, and systemic lupus erythromatosus (SLE). Antiphospholipid syndrome has the hallmark presence of lupus anticoagulant (LA) or anticardiolipin antibody (ACA) activity (Shapiro, S. S. (1996) Ann. Rev Med. 47: 533-53). Antiphospholipid syndrome is defined as a clinical disorder with recurrent arterial and venous thrombotic events, pregnancy wastage and/or thrombocytopenia in the presence of the lupus anticoagulant and/or moderate to high positive anticardiolipin assay. Both a primary form, in subjects without clinically or serologically evident autoimmune disorders, and a secondary form, usually in subjects with systemic lupus erythematosus, is recognized.

The presence of antiphospholipid antibodies mainly has been demonstrated in subjects with systemic lupus erythematosus with the prevalence ranging between 20% and 50%. Subjects with SLE manifest what is described as secondary APS, which results in heightened neurological disorders and arterial events. Without wishing to be bound by any one theory, the exact mechanism by which antiphospholipid antibodies cause clinical manifestations of the syndrome is unclear. Strokes, often preceded by transient ischemia attacks, are the most frequent arterial events encountered. Skin ulceration and cutaneous necrosis and infarction are often seen.

Thrombosis may be present in small, medium, or large venous or arterial sites. The presentation is episodic and unpredictable. Venous thrombosis of a leg or arm, renal vein thrombosis, the Budd-Chiari syndrome, pulmonary embolism, Addison's disease, retinal, sagital, pelvic, mesenteric, portal and axillary vein thrombosis have all been described. When an arterial site is involved, the manifestations may vary between the clinical features of a stroke or transient ischemic attack. When other arterial vascular beds are affected, such as the retinal, coronary, brachial, mesenteric, renal (interlobular arteries, arterioles and glomerular capillaries) and dermal arterioles, the clinical presentations are directly related to involved site.

Some subjects may present with recurrent pregnancy losses often, but not always, in late second or third trimester of gestation. Nervous system disorders also are a consequence of APS. Most neurologic abnormalities are consequent to cerebrovascular thrombosis, which result in reversible or fixed focal deficit. The neurological manifestations of the subject with APS are much wider transient ischemic attacks, cerebral infarcts and cerebral venous thrombosis. Other neurologic presentations include epilepsy, transverse myelopathy, Guillain-Barre syndrome and chorea. APS also is associated with renal vein thrombosis, Addison's disease, gut ischemia, Budd-Chiari syndrome, thrombocytopenia, autoimmune hemolytic anemia, idiopathic thrombocytopenic purpura, cardiac valve abnormalities (insufficiency mitral and aortic) and Libman-Sacks endocarditis. Further, dermatologic manifestations are extremely frequent, including livedo reticularis, leg ulceration, distal cutaneous ischemia or necrosis, superficial thrombophlebitis, blue-toe syndrome, splinter hemorrhage and porcelain-white scars are also seen.

Laboratory diagnosis is based on the presence of antiphospholipid antibodies, such as LA antibodies and ACA antibodies. The lupus anticoagulant is a type of antiphospholipid antibody, an immunoglobulin or immunoglobulin-like molecule that prolongs clotting time in vitro because phospholipids present in the plasma agglutinate, thereby preventing their participation as cofactors in coagulation steps. Its in vitro action appears to be the inhibition of the conversion of prothrombin to thrombin.

Since phospholipids are not very antigenic, the true antigen for the lupus anticoagulant antibody is a plasma protein that binds to phospholipids. The heterogeneity of the lupus anticoagulant can, therefore, be explained by the concept that the lupus anticoagulants are a family of antiphospholipid-plasma antibodies, with subgroups defined by both the phospholipids and plasma protein involved. Accordingly, no lupus anticoagulant assay is 100% sensitive. Therefore, the following criteria are required for a positive lupus anticoagulant assay: (1) prolonged activated partial thromboplastin time (aPTT), prolonged dilute Russell's Viper Venom time (dRVVT), prolonged kaolin clotting time, and prolonged dilute prothrombin time (dPT); (2) failure to correct the test by mixing subject plasma with normal plasma (suggesting a clotting inhibitor is present); and (3) normalization of the assay with freeze-thawed platelets or phospholipids.

Because antiphospholipid antibodies cross-react with other negatively charged phospholipids, cardiolipin can serve as a representative antigen in the system. Anticardiolipin antibodies are one of the few autoantibodies for which assays allow the identification and quantification of specific isotypes (IgG, IgM and IgA). The IgG isotype can be a major predictor of thrombosis and pregnancy loss while the IgM class was associated especially with hemolytic anemia in addition to thrombosis. Aside from the identification of different isotypes, antibody titer can be a useful predictor of pathogenicity (even though it is still not clear that antibody titer is the best or the only predictor). The higher-titer of IgG anticardiolipin antibody (>40 GPL) correlates strongly with thrombosis and fetal loss. Most subjects with antiphospholipid syndrome have medium to high IgG anticardiolipin antibody levels with or without other isotypes.

Both lupus anticoagulant and anticardiolipin antibodies are associated with each of the clinical manifestations of the antiphospholipid syndrome. There is much controversy between the relation of ACA and LA; thus the assay may be positive for one, negative for other, or positive for all. The present invention provides kits and methods that allow for streamlined testing for antiphospholipid antibodies, in that test plasma samples can be tested for one or more coagulation assays known in the art and described herein, using one high phospholipid reagent that markedly decreases the likelihood of false positives.

Systemic lupus erythematosus (SLE) is a febrile, inflammatory, multi-system disease that is best characterized by a number of features. Clinically, it is an unpredictable, remitting and relapsing disorder of acute and insidious onset. It may involve any organ in the body, but it principally affects the skin, kidneys, serosal membranes, joints and the heart. Anatomically, all the sites involved in the disorder have vascular lesions comprising fibrinoid deposits. Immunologically, the disorder involves a bewildering array of autoantibodies and especially antinuclear antibodies.

The clinical manifestations of SLE are so varied that it bears a great deal of similarity to a plethora of other autoimmune disorders, including rheumatoid arthritis and polymyositis, among many others. This heterogeneity has necessitated the use of a list of diagnostic criteria to be fulfilled before a definitive diagnosis of the disorder can be attained. There are at least 14 criteria that can be examined; if four or more of these criteria are present, then SLE is indicated (Cohen, S. A. et al., (1971) Clin Exp Immunol. 8(4): 551-61). These criteria include facial erythema, discoid lupus rash, Raynaud's phenomenon, alopecia, photosensitivity, oral nasal or pharyngeal ulceration, arthritis without deformity, LE cells, false positive assays for syphilis, proteinurea (>3.5 g/day), pleuritis, pericarditis, psychosis, convulsions hemolytic anemia, leukopenia and thrombocytopenia.

Pathogenesis of the disorder is of an autoimmune type and involves antiphospholipid antibodies and anti-nuclear antibodies, among others. Anti-nuclear antibodies are targeted against soluble and particulate nucleoproteins of double-stranded and single-stranded DNA, single-stranded and double-stranded RNA, as well as a saline extractable nuclear constituent (Sm antigen). Additionally, antibodies have been identified against the mitochondria, ribosomes, lysosomes, a soluble cytoplasmic fraction, red cells, white cells, platelets and blood clotting factors (Wiedermann, G. and Meischer, P. A., (1965) Ann. NY Acad. Sci. 124(2): 807-15). SLE subjects also develop antiphospholipid antibodies, and this is associated with increased arterial and venous thrombosis, thrombocytopenia, neurologic disorders, and recurrent fetal loss. Given the presence of all these autoantibodies, remarkably little is known about the mechanisms of their emergence and the diagnosis and treatment of this disease is still dependent on numerous factors.

As used herein, an "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, such as Fab, Fab', F(ab')(2), Fv, single chain (ScFv), mutants thereof, fusion proteins, humanized antibodies, and any other modified configuration of the immunoglobulin molecule that comprises an antigen recognition site of the required specificity.

As used herein, the term "antiphospholipid antibodies" refers to immunoglobulin or immunoglobulin-like molecules that have specificity for a protein that binds phospholipids. Such proteins include β2-GP1, thrombin, prothrombin, thrombomodulin, tissue plasminogen activator (tPA), cardiolipin, high- and low-molecular weight kininogens, complement proteins, Factor XII, protein C, protein S, and annexin V. Therefore, antiphospholipid antibodies encompass lupus anticoagulants, anti-β2-GP1 antibodies, anti-protein C antibodies, anti-protein S antibodies, anti-complement antibodies, anticardiolipin antibodies, anti-thrombin antibodies, anti-prothrombin antibodies, anti-thrombomodulin antibodies, anti-tPA antibodies, anti-Factor XII antibodies, anti-kininogen antibodies, and anti-annexin V antibodies, but are not limited to these examples.

The term "lupus anticoagulant" can also be referred to in the context of the present invention as "coagulation inhibitors", "lupus inhibitors", or "circulating inhibitors".

As used herein, the term "plasma" generally refers to a solution comprising proteins and having procoagulant activity when combined with, for example, a dilute prothrombin time (dPT) reagent, a dilute Russell's viper venom time (DVV) reagent, or with an activated partial thromboplastin reagent (aPTT). Proteins in plasma preferably include, but are not limited to, blood clotting-factors involved with the extrinsic pathway (e.g. Factor VII) and/or with the intrinsic pathway (e.g. Factors XII, XI, IX and/or VIII), blood-clotting factors common to both pathways (e.g. Factors X, II and/or V), thrombin, and fibrinogen. Plasma can also preferably include other plasma proteins, sugars, and/or salts.

Plasma can be whole plasma that is obtained from humans or other animals, preferably from a human subject. Plasma can also be a plasma derivative that has procoagulant activity and is derived from one or more whole plasmas. The plasma derivative can be, for example, a plasma fraction or plasma that has been purified or otherwise treated to remove some protein, sugar, salt or other components thereof. Plasma can alternatively be a plasma substitute formed from components obtained from separate sources, including natural or synthetic components, and having procoagulant activity. Exemplary synthetic components include plasma proteins that are substantially isolated and/or purified from natural sources and plasma proteins that are prepared using recombinant technology. Whole plasmas, plasma derivatives and plasma substitutes are commercially available and/or can be prepared using methods presently known and/or later developed in the art.

Plasma samples can be obtained from blood derived from a single subject, or from blood pooled from numerous sources ("pooled normal plasma" or PNP). PNP can provide a reference range that minimizes variations possible with individual samples.

A "control plasma sample" can be obtained from blood derived from a subject or subjects who have low or absent levels of antiphospholipid antibodies or otherwise are not at risk for, or are not suffering from, an autoimmune disorder characterized by the presence of antiphospholipid antibodies. Such control plasma samples can also be referred to herein as "negative control plasma samples."

Alternatively, a control plasma specimen can be obtained from blood derived from a subject who is known to suffer from an autoimmune disorder characterized by the presence of antiphospholipid antibodies, and such samples can be referred to in the context of the present invention as a "positive control plasma samples." Control samples derived from individual or pooled plasma can be characterized and standardized for repeated use in the kits and methods used and described herein.

Accordingly, a "test plasma sample" is obtained from blood derived from a single subject who is at risk for or is suffering from an autoimmune disorder characterized by the presence of antiphospholipid antibodies. Test and control samples can be whole blood, plasma, serum, or comprise isolated immunoglobulins. Preferably, plasma is used in the kits and methods of the present invention. Of note, plasma should be anticoagulated prior to use to eliminate or substantially reduce the amount of clotting factors already present in the plasma and clotting reactions that occur prior to using the methods and kits of the invention. Useful anticoagulants can include, but are not limited to, ethylenediamine tetraacetic acid (EDTA), ethylene glycol tetraacetic acid (EGTA), heparin, coumadin, warfarin, danaparoid, argatroban, and hirudin. The plasma used in the kits and methods of the invention can also be citrated using, for example, trisodium citrate. The dihydrate form of trisodium citrate is preferred.

One preferred plasma that can be used as the coagulation control plasma samples is human plasma. The human plasma sample can be a control human plasma sample or a test human plasma sample. Control human plasmas, as defined above, can include plasmas obtained from subjects without clotting deficiencies, or alternatively, obtained from subjects not at risk for or not suffering from an autoimmune disorder characterized by the presence of antiphospholipid antibodies and a decreased rate of coagulation. If evaluated using a dPT assay with a thromboplastin reagent having an International Sensitivity Index of about 2, normal human plasmas would preferably have a clotting time ranging from about 9 seconds to about 14 seconds, preferably from about 11 seconds to about 13 seconds, and would most preferably be about 12 seconds. If evaluated using an aPTT assay using an aPTT reagent that is moderately sensitive to heparin and to lupus anticoagulant (e.g. Dade Bering aPTT-FSL, Dade Behring, Deerfield, Ill.) and a suitable coagulation analyzer (e.g. Amelung AMAX CS-190), normal human plasmas would preferably have a clotting time ranging from about 22 seconds to about 32 seconds.

Normal human plasmas can be frozen at a temperature ranging from about −50° C. to about −100° C. for storage. If frozen normal human plasmas are employed as starting materials, they are preferably thawed in an environment (e.g. such as a water bath) at a temperature of about 37° C. prior to use in connection with the kits and methods of the present invention. The control human plasmas can preferably be pooled normal human plasmas (PNP) prepared by the pooling of at least about 5, preferably at least about 10 plasma specimens obtained from individuals or other humans without clotting deficiencies or from subjects not at risk for or not suffering from an autoimmune disorder characterized by the presence of antiphospholipid antibodies and a decreased rate of coagulation. The normal human plasmas can be pooled prior to freezing, or, if frozen prior to pooling, after thawing.

Test plasma samples can, in general, be any plasma that is deficient with respect to coagulation rate as compared to normal plasma, or derived from subjects at risk for or suffering from an autoimmune disorder characterized by the presence of antiphospholipid antibodies and a decreased rate of coagulation. The deficiency can be an increased clotting time or a decreased clotting time, relative to normal or control plasma samples. Test plasma samples can be plasma collected from individuals, other humans or non-human mammals having naturally occurring clotting deficiencies or undergoing anticoagulant treatment. The test plasma samples can also, however, have clotting deficiencies that are artificially induced by treatment of the plasma in vitro using methods known in the art.

Exemplary test plasma samples include activated plasmas, which typically have an increased rate of coagulation and are employed in a coagulation control composition to decrease the clotting time of the control, and Factor-deficient plasmas, which typically have decreased rates of coagulation and are employed in a coagulation control composition to increase the clotting time of the control. As used herein, the term "activated plasma" refers to a test plasma sample having increased levels of clotting Factor Xa relative to normal plasma. An activated plasma can be human plasma or non-human plasma, such as non-human human plasma or non-human mammalian plasma. Activated human plasma is a preferred activated plasma.

The activated plasma can be activated for the extrinsic pathway (e.g. using thromboplastin and/or other known extrinsic-pathway activating agents) and/or for the intrinsic pathway (e.g. by exposing the plasma to intrinsic-pathway activating agents such as negatively charged moieties with a large surface area). Exemplary intrinsic-pathway activating agents include organic acid salts such as salts of ellagic acid, and silica-containing species such as micronized silica, kaolin, Celite and glass-wool.

The present invention also encompasses the use of "Factor-deficient plasma," which refers to a test plasma sample that is deficient in one or more clotting factors selected from the group consisting of Factor II, Factor VII, Factor IX and Factor X. Factor-deficient plasmas can be naturally occurring and obtained by collection from subjects, or alternatively, can be induced in vitro by removing clotting factors from normal plasma by methods known in the art. Factor-deficient plasmas can be prepared by contacting the plasma with absorbents such as aluminum hydroxide, barium chloride, barium citrate, and/or barium sulfate, among others. Other methods can also be employed for preparing factor-deficient plasmas. For example, a Factor VII-deficient plasma can be prepared using anti-Factor VII antibodies and immunoaffinity purification protocols.

The plasma, preferably a human plasma, is generally present in an amount ranging from about 25% to about 99.55%, more preferably in an amount ranging from about 50% to about 99.5%, even more preferably in an amount ranging from about 75% to about 99.5%, and most preferably in an amount ranging from about 78% to about 99.8% by volume, relative to total solution volume. The particular amount of plasma (e.g. human) will depend, as discussed below, on the types and quality of plasmas (e.g. control and/or test plasmas), on the presence of other types of plasmas (e.g. non-human mammalian plasmas), and the type of control composition being prepared (e.g. derived from a subject having low or undetectable levels of antiphospholipid antibodies, or alternatively, from a subject having high levels of antiphospholipid antibodies).

Non-human mammalian plasmas can be purified prior to use in connection with the present invention. Frozen non-human mammalian plasma, such as frozen bovine plasma, is either prepared or obtained, for example, from a commercial source. The frozen plasma can then be thawed in an environment maintained at a temperature ranging from about 2° C. to about 8° C. Certain plasma constituents (e.g. plasma proteins) are not soluble at these cold temperatures, and as such, will fall out of solution, as precipitants and/or as particulates. The particulates formed in the thawed plasma can then be removed therefrom by any suitable separation means, such as filtration or centrifugation. These freezing and thawing steps can be repeated once or several times, by refreezing the partially-purified plasma, rethawing the refrozen plasma at a temperatures ranging from about 2° C. to about 8° C., and then removing any additional particulates formed in the rethawed plasma. The resulting purified plasma is then advantageously free of constituents (e.g. plasma proteins) that are insoluble at lower temperatures. Significantly, thawing at the recited cold temperatures allows for removal of such particulates prior to lyophilization. If the frozen plasma is thawed at higher temperatures, the particulates would have remained in solution and would have been included in the lyophilized composition. When such lyophilized compositions are subsequently reconstituted, many of those particulates are not resolubilized, and can, therefore be undesirably present as particulates in the reconstituted control composition.

For example, kits and reagents comprising the kits of the present invention can preferably include buffers and bulking agents. The buffer can be any compatible buffer, and preferably has a pKa ranging from about 6 to 8, more preferably from about 7 to 8, and most preferably of about 7.1 to about 7.6. Preferred buffers include for example, N-2-hydroxyethyl piperazine-N-2-ethanesulfonic acid (HEPES), and 3-(N-morpholino)-propanesulfonic acid (MOPS), with HEPES being a most preferred buffer. Other exemplary buffers include Tris, N,N-bis-(hyrdroxyethyl)-2-aminoethanesulfonic acid (BES), N-tris-(hyrdroxymethyl)-methyl-2-aminoethanesulfonic acid (TES), 3-[N-tris(hydroxymethyl)methylamino]-2-hydroxypropanesulfonic acid (TAPSO) and 3-[N-tris-(hydroxymethyl-methylamino]-propanesulfonic acid (TAPS), among others. The amount of buffer included can be generally based on dPT, DVV, and/or aPTT times. Bulking agents that can be included in the control composition include glycine, glucitol, mannitol, sorbitol, lactose, dextrose and the like. Glycine is a preferred bulking agent. Bulking agents are preferably included in an amount ranging from about 0.5% to about 5%, by weight, and are most preferably at about 1% by weight, relative to total solution weight assuming a solution density of about 1 g/ml. That is, 1% bulking agent by weight is equal to 10 g bulking agent per liter of solution.

Stabilizers, preservatives, and other components known in the art can also be employed in the reagents comprising the assay kits of the present invention. Stabilizers that may be useful include, for example, Goods buffers, Tris, bovine serum albumin (BSA), piperazine-N,N-bis(2-ethane-sulfonic acid, 1,5 sodium salt (PIPES), imidazole, 3-(N-morpholino)-2-hydroxypropanesulfonic acid (MOPSO), MOPS, BES, TES, HEPES, TAPSO, TAPS, 3-[N-bis(hydroxyethyl)amino]-2-hydroxypropanesulfonic acid (DIPSO), piperazine-N,N'-bis(2-hydroxypropanesulfonic acid (POPSO); N-hydroxyethyl piperazine-N'-2-hydroxypropanesulfonic acid (HEPPSO), tricine and bicine. Preservatives that may be helpful for preventing the growth of microorganisms, such as antifungal and antibacterial compounds, may also be included in the composition. Exemplary preservatives include organic acids such as propionic acid, sodium azide, Fungizone®, thimerosal, BHA, BHT and preformulated multiactivity formulations such as ProClin. The concentrations of these additional components can be determined and optimized by one of skill in the art. The total volume contribution of such additional components to a coagulation control solution can, in general, range from about 0-3%, and preferably from about 0-2% by volume, relative to total solution volume. Reagents included in the kits of the present invention can typically include about 1% of such other constituents, by volume, relative to total solution volume.

Reagents prepared as described above can be lyophilized according to methods known in the art. For example, freezing at a temperature and under vacuum for a period of time sufficient to form the lyophilized reagents can lyophilize the compositions. The temperatures, vacuum and period of time are not narrowly critical, but lyophilization can be generally performed as follows. The compositions are frozen to a deep freeze temperature typically ranging from about −60° C. to about −20° C., without vacuum, for a period of time ranging from about 2 hours to about 24 hours. A vacuum is then applied, preferably ranging from about 10 millitorr to about 200 millitorr absolute pressure. The shelf temperature can then be raised somewhat, typically to a temperature ranging from about 0° C. to about 25° C., for a period of time sufficient to lyophilize the composition. The lyophilization can be performed by first deep-freezing the composition in a chamber to a temperature of about −40° C., without vacuum, for a period of about 4 hours, and then drawing a vacuum of less than about 200 millitorr in the chamber and subsequently raising the temperature, preferably to about 25° C. for a period sufficient for the product to reach about 25° C. for about 4 hours. A vacuum of less than about 200 millitorr is subsequently applied, and the shelf temperature is raised to about 25° C. for a period of time sufficient to lyophilize the solution. The lyophilized reagents are preferably sealed under vacuum. The lyophilized reagents can be stored, prior to reconstituting, for about 2 years at temperatures from about 2° C. to about 8° C.

The lyophilized reagents can be reconstituted using water, an appropriate buffer, or other reconstituting solution. Preferably, the volume of reconstituting solution is sufficient to form reagents comprising the various plasmas at the aforementioned relative volumes. If a larger or smaller reconstituting volume is desired, prior to lyophilization the amounts of the various plasmas present in the as-prepared reagents should be adjusted accordingly to form a post-lyophilization, reconstituted reagent comprising the various plasmas at the aforementioned relative volumes.

Kits for assessing hemostatic potential according to the present invention contain at least one procoagulant test reagent. Additional components of the reagent or kit can include a low level of phospholipids, metal salt or ions, and anticoagulant pathway activator, if desired. In the kit, the components can all be provided in separate containers, or mixed together in any combination in one or more containers. If phospholipids are added, they can be any suitable phospholipid or combination of phospholipids, including one or more of phosphatidylcholine, phosphatidylethanolamine and phosphatidylserine, which can be provided at a ratio of approximately 5 to 30 mole percent phosphatidylethanolamine, 1 to 10 percent phosphatidylserine and the remainder phosphatidylcholine. These phospholipids can be prepared in a variety of ways to yield liposomes of various sizes, such as by sonication. Alternatively, the phospholipids can be provided as free phospholipids.

Phospholipids can be provided at a concentration that is not rate limiting, e.g. at a concentration of from about 10 to about 300 micromolar, and preferably in the range of from about 50 to about 200 micromolar. When a low level of phospholipids is added to the procoagulant test reagent, tissue factor or other procoagulants can be provided at a concentration of about 10 picomolar or less, about 8 picomolar or less, or preferably about 6 picomolar or less. The concentration can be about 3 picomolar or less, though whatever the concentration of tissue factor, it should allow for hemostatic potential assessment as set forth herein. If it is desired to add thrombomodulin, it can be provided at a concentration of about 30 nanomolar or less, preferably in a range of from about 5 to about 20 nanomolar. If a metal salt is to be added, it can be provided in a reagent or kit at a concentration of from about 5 to about 50 mM, preferably from about 15 to about 35 mM. Such metal salts include salts of calcium or magnesium. A compatible buffer or solution that can be used in the kits and methods of the invention preferably contains calcium. Exemplary calcium salts include calcium chloride and calcium phosphate. These calcium salts can be advantageously added to the compatible buffers that can comprise additional agents, such as bulking agents or other diluents/excipients.

Procoagulants that can be added to procoagulant test reagents defined by the present invention include, but are not limited to, Russell's viper venom, Taipan snake venom, textarin, ecarin, thrombin, kaolin, silica, ellagic acid, and tissue factor (also known in the art as thromboplastin and used interchangeably in the context of the present invention). Other procoagulants can include *Agkistrodon contortrix* venom, commonly referred to as Protac® (Pentapharm, Basel, Switzerland), or related species such as *A. piscovorus, A. bilineatus, A.C. laticinctus*, and *A.C. moccason*. The snake venoms can be used in a diluted but unfractionated form or, preferably, can be used in a fractionated form utilizing isolated venom components. Preferably, the kits or reagents of the present invention also contain supplemental components such as suitable buffers and preservatives. In addition, the procoagulant test reagents can preferably contain polybrene or another similar agent to reverse the effect of any heparin that may be present in the test samples, or which may be added in preincubation reagents. A substrate conversion reaction rate can be determined by the coagulation time or by the time required for the conversion of a chromogenic substrate to a colored product. The conversion rate obtained is compared with values obtained with results on control plasma samples.

Phospholipid substrates include phospholipids such as, but not limited to, phosphatidylserine, phosphatidylcholine, phosphatidylethanolamine, phosphatidylinositol, cardiolipin, phosphatidic acid, and combinations thereof, but can also comprise phospholipid coated solid substrates, such as phospholipid coated microtiter plates, phospholipid coated silicon wafers, phospholipid coated beads, and phospholipid suspensions. Alternatively, cells or cell lines that display surface anionic phospholipids, such as, for example, platelets, endothelial cells, such as human umbilical vein endothelial cells (HUVEC) and human microvascular endothelial cells (HMEC), and trophoblasts, may supply phospholipids. A phospholipid substrate may be present as free phospholipids, or sonicated into liposomes or arranged hexagonally. As used herein, the term "high phospholipid substrate" refers to an assay kit reagent or a reagent used in the methods of the invention that comprises a higher concentration of phospholipids, as compared to the low level of phospholipids that can be present in the procoagulant test reagents described herein. The "high phospholipid substrate" is used in the confirmatory steps of the methods of the invention to demonstrate the phospholipid-dependent nature of any antiphospholipid antibody species or anticoagulant present in plasma samples that tested positive during the screening step.

"High phospholipid" is at least about 1 mg/ml phospholipid concentration, and "low phospholipid" is about 50 µg/ml phospholipid concentration or less.

The kits and methods of the present invention can also include cofactors. For example, β2-GP1 is a serum protein that is required for antiphospholipid antibody binding to phospholipids (Roubey, R. A., (1994) Blood 84: 2854-67). Other proteins, such as for example, prothrombin, annexin V, protein C, protein S, and cardiolipin can also be used as cofactors. In addition to proteins, primary and cultured cells can also be used as cofactors.

Most coagulation assays involve end-point assays in which, after the blood sample is incubated with exogenous reagents, the time of clot formation is measured. The rate of coagulation may also be used as a measure of coagulation. Examples of coagulation assays include, but are not limited to, assays detecting the presence of cardiolipin antibodies, activated partial thromboplastin time assays (aPTT), dilute prothrombin assays (dPT), activated clotting time assays (ACT), and dilute Russell's Viper Venom time assays (also known in the art as dRVVT). Most coagulation assays comprise a screening step, which is performed on a test plasma sample in the presence of a procoagulant test reagent comprising a low level of phospholipids, and followed by a confirmatory step. The confirmatory step is performed with the same test plasma sample and procoagulant test reagent, but also comprises a high phospholipid substrate. In the context of the present invention, the high phospholipid substrate can be used in more than one coagulation assay to confirm the presence of antiphospholipid antibodies and diagnose autoimmune diseases characterized by the presence of antiphospholipid antibodies and a decreased rate of coagulation.

The kits and methods of the present invention provide reagents that allow for streamlined testing for antiphospholipid antibodies. A key feature over the prior art is that some of the same reagents are used in each coagulation assay. The use of a single high phospholipid substrate in the kits and methods of the invention thereby substantially decreases or even eliminates the likelihood of false positives in the confirmation step of coagulation assays, which must be performed in the presence of a high phospholipid substrate to demonstrate the phospholipid-dependent nature of the antiphospholipid antibodies. Each assay can be performed simultaneously, or in succession, using the same high phospholipid substrate with different procoagulant test reagents tailored for each coagulation assay. Alternatively, the same coagulation assay could be performed more than once, e.g., in triplicate, to determine the reliability of results obtained from the coagulation assay.

The aPTT test is used to evaluate the intrinsic coagulation system (including Factors I, II, V, VIII, IX, X, and XII). In the aPTT test, the intrinsic coagulation system is activated by the addition of phospholipid, and a procoagulant such as ellagic acid, kaolin, thromboplastin, or micronized silica, in the presence of calcium ions, is added to plasma samples. Formation of the prothrombinase complex on the phospholipid surface allows for conversion of prothrombin to thrombin with subsequent clot formation. The time, in seconds, that is required for this reaction to occur is the "activated partial thromboplastin time." The aPTT assay should be performed first on plasma samples that have not received any anticoagulant drugs, such as heparin, hirudin, or the like.

The dPT assay is used to evaluate the integrity of the extrinsic coagulation pathway, which includes Factors I, II, V, VII, and X. The dPT assay is performed by adding thromboplastin, tissue factor, or prothrombin, and calcium ions to the plasma sample and measuring the time to clot formation. If the clotting time is prolonged, decreased, or delayed, there is a defect in the extrinsic coagulation pathway, possibly through antiphospholipid antibodies.

The DVV (or dRVVT) assay uses Russell's Viper Venom that directly activates Factor X to Factor Xa in the presence of phospholipids in calcium, converting fibrinogen to fibrin and leading to detectable clot formation in plasma. This direct activation bypasses the Contact and Intrinsic Factors in the coagulation cascade, thereby excluding interference from deficiencies in Factors VIII, IX, XI, and XII, or their respective inhibitors. A prolonged clotting time can indicate the presence of antiphospholipid antibodies.

Another assay is the textarin/ecarin time assay. The textarin/ecarin ratio is an assay based on the differential dependence of snake venom on phospholipids to activate the coagulation pathway. Various snake venoms contain enzymes that specifically affect the coagulation pathway by catalyzing the conversion of prothrombin to thrombin, and/or to the active intermediate meizothrombin. Because of their direct effect on prothrombin activation without dependence on the upstream clotting factors, snake venom can be used as reagents in highly specific assays for the detection of antiphospholipid antibodies. Three groups of snake venoms are described in the art. Venom from group I snakes, such as *Bothrops* or *Echis* species, convert thrombin to meizothrombin, independent of factor V, phospholipids or calcium ions. Group II snake venom, from *Notechis* species, contains activators of prothrombin, which are highly stimulated by Factor Va, phospholipids, and calcium. Group III venom, from *Pseudonaja* and *Oxyuranus* species, contains activators of prothrombin that are strongly dependent on phospholipids and calcium for activity, but minimally dependent on Factor Va.

Textarin, from *Pseudonaja textiles*, directly activates prothrombin in the presence of Factor V, calcium and phospholipids, whereas, ecarin, a venom from *Echis carinatus* activates prothrombin to form meizothrombin in the absence of phospholipids. Textarin time is prolonged by antiphospholipid antibodies, due to its phospholipid-dependence, and is therefore an extremely sensitive assay for LA. Antiphospholipid antibodies do not affect ecarin time; therefore mixing textarin and ecarin in ratios of about 0.8 to about 1.2 can be a very sensitive and specific assay for antiphospholipid antibodies, such as lupus anticoagulants. Factor V deficiency and specific inhibitors of factor V will cause prolongation of the textarin time, but these appear to be the only factor deficiencies which cause a false positive. Specific factor inhibitors or deficiencies, (except prothrombin) do not affect the ecarin time because ecarin acts directly on prothrombin, independent of all other factors.

Although performed routinely, all of the currently available coagulation assays have inherent limitations that can decrease the utility of such tools for monitoring coagulation. Most of the limitations relate to the fact that no single assay can reliably and reproducibly detect all antiphospholipid antibodies. Therefore, these tests are routinely performed together, sometimes in concert, to confirm a positive result obtained in another coagulation assay. The available coagulation assays known in the art also suffer from technical caveats such as false positives, wherein a positive result in a first screening step does not correlate to or presents fluctuations in values/rates obtained from a second confirmatory step. These technical caveats are usually derived from differing activities of the reagents that can be introduced through manufacturing methods, experimental error, or degradation of the reagent. The present invention provides novel and efficient methods that circumvent these caveats and that can decrease the likelihood of false positives during testing.

Clot formation can be monitored and detected using spectrophotometric methods, encompassing detection of optical density, chemiluminescence, and chromogenic markers. Prolongation of the clotting time may be measured in various ways (e.g., photometrically or chromogenically). When clotting is measured chromogenically, a substrate for a component of the coagulation cascade that is influenced by protein S activity may be added to the assay. An exemplary chromogenic substrate would be a substrate for thrombin (e.g., H-D-HHT-Ala-Arg-pNA.2AcOH, Spectrozyme®TH from American Diagnostica Inc, Stamford, Conn.).

Coagulation rates are measured using coagulation analyzers. Coagulation analyzers measure the fibrinogen concentration in plasma, which can be determined quantitatively by, for example, kinetic endpoint testing methods (using thromboplastin) and the Clauss clotting method (using high levels of thrombin). The determination of clot formation by kinetic endpoint testing methods is based on addition of a commercially prepared thromboplastin reagent to undiluted plasma, followed the measurement of turbidity increase. By using the clotting factors provided by the native plasma, the kinetic endpoint method very closely approximates the in vivo reaction between human thrombin and fibrinogen. The Clauss test method involves measuring the rate of conversion of fibrinogen to fibrin in a diluted sample in the presence of excess thrombin. Under these conditions, fibrinogen content is rate limiting, and the clotting time can be used as a measure of the concentration of the fibrinogen. Clotting time is inversely proportional to the level of fibrinogen in plasma.

Clot detection by coagulation analyzers commonly involves an electromagnetic-mechanical system. In some machines, the coagulation analyzer monitors oscillation of a probe within the detection cuvette containing the thrombin and diluted plasma sample. When the oscillation of the probe is stopped by clot formation, the sensor registers the time in seconds. The time is expressed as fibrinogen concentration as generated from a standard curve. In other machines, a coagulation analyzer can detect clot formation by mechanical endpoint detection using a device called a "fibrometer." A fibrometer detects changes in electrical conductivity and usually includes one stationary probe and one moving probe.

Another method includes photo-optical endpoint detection, where changes in optical density of the test sample are monitored. Fibrin formation causes the plasma sample to become opaque and, as a result, the amount of light that is detected decreases. Other coagulation analyzers monitor blood flow through a channel within the machine. The analyzer then detects an impediment of blood flow contributed by clot formation, such as by optical light-emitting diode (LED) sensors. As clot formation begins, blood flow is impeded and the movement slows. The instrument recognizes that the clot endpoint has been achieved when the movement decreases below a predetermined rate. Other methods include, but are not limited to, immunologic endpoint detection, nephlometric endpoint detection and chromogenic endpoint detection. In chromogenic endpoint detection, a chromophore is attached to a substrate. Cleavage of the chromophore by coagulation proteins is detected by measuring optical absorbance at a selected wavelength.

Coagulation analyzers are available from Diagnostica Stago (Asnieres, France) and Sysmex (Mundelein, Ill.), among others. Coagulation analysis can be optimized and/or semi-automated or completely automated for high-throughput analysis when many samples are present. In manual coagulation analysis, all reagents, samples, and timing are controlled by the person performing the assay. Semi-automated systems have automated detection of the clot, however reagents and samples are added manually. Automated systems automatically control reagent pipetting, timing, and clot detection.

After detecting the presence of antiphospholipid antibodies through the methods of the invention described herein, the antibodies can be further purified and/or characterized by methods well known in the art, such as binding to protein A- or protein G-coated agarose beads, labeling the antibodies with markers such as biotin, radioisotopes such as 125I, 131I, 35S, 32P, among others, chromogenic labels, such as alkaline phosphatase or horseradish peroxidase coupled to chemiluminescent substrates, or NBT/BCIP (nitro blue tetrazolium chloride/bromo-4-chloro-3-indolyl phosphate). Enzyme-linked immunosorbent assays (ELISA), immunoprecipitation, and Western blotting can be used to identify the specific species of antiphospholipid antibodies present in the test plasma sample. The antibody can be labeled with other labels selected from the group consisting of an enzyme, a dye, a fluorescent tag label, a hapten and a luminescent label. The fluorescent tag can be selected from fluorescein, rhodamine, luciferase and green fluorescent protein. Dyes can be selected from the group consisting of phycoerythrin, phycocyanin, allophycocyanin, Texas Red and o-phthaldehyde. The enzyme can be alkaline phosphatase, or horseradish peroxidase. Antiphospholipid antibodies can also be bound to any solid support that is routinely used in the art, for example a microtiter plate, a polystyrene bead, an agarose bead, a test tube or a dipstick.

The invention will now be further described by way of the following non-limiting Examples, given by way of illustration of various embodiments of the invention and are not meant to limit the present invention in any fashion.

EXAMPLES

Example 1

Lupus Anticoagulant Testing Using ACTICLOT® dPT™

Experiments were performed to show that tests currently in use, such as the two-step DVVtest® and DVVconfirm®, can be reformatted into the dPT-like three component system of the invention. The high phospholipid substrate of the dPT can be used to confirm a positive LA identified with the DVVtest® activator. Thus, in the reformatted DVV assay, the same phospholipid substrate is used in both the screening and confirmatory tests. This eliminates the problems encountered using the current DVV format.

Table 1 shows the results of LA testing using ACTICLOT® dPT™ (American Diagnostica Inc). The protocol was performed according to manufacturer's instructions. Clotting times were determined in ACL300 coagulation analyzer (Instrumentation Laboratories Ltd., Milan, Italy).

TABLE 1

| SAMPLE | dPT test (sec) | dPT test + PL (sec) | T/C |
|--------|----------------|---------------------|------|
| PNP    | 31.6           | 31.1                | 1.01 |
| LA     | 84.1           | 39.2                | 2.14 |

The RVV activator was made by using the DVVtest® reagent at twice the concentration. This was achieved by reconstituting the lyophilized DVVtest® reagent with one-half the normal volume of water. Thus, for a DVVtest® reagent that normally requires adding 2 ml of water, adding 1 ml of water makes the new DVV activator. The buffer and the high phospholipid substrate are the same as those currently used in dPT assays.

The assay is performed by mixing the reagents as follows: the Screening test contains 100 μl of plasma, 50 μl of buffer, and 50 μl of 2×DVV activator. The Confirmatory test contains 100 μl of plasma, 50 μl of high phospholipid substrate, and 50

μl of 2×DVV activator. Clotting times were determined using manual or automated coagulation instruments, such as ST4 and STA Compact (Diagnostica Stago, Asnieres, France), ACL300, and CA7000 (Sysmex, Milton Keynes, UK).

Example 2

Comparison of Reformatted and Unformatted dPT Screening Methods

A comparison between the reformatted three-reagent DVV of the current invention and the old two-reagent system was performed using the DVVtest® and DVVconfirm® as an exemplary two-reagent system. Clotting times were determined in ACL300 coagulation analyzer and are shown in Table 2.

TABLE 2

| SAMPLE | Reformatted Protocol | | | DVVtest ® and DVVconfirm ® Protocol | | |
|---|---|---|---|---|---|---|
| | DVV Screen (sec) | Confirm | T/C | DVVtest | DVVconfirm | T/C |
| PNP | 31 | 25 | 1.24 | 29.3 | 29.5 | 0.99 |
| LA | 77 | 38 | 2.03 | 80.5 | 34.6 | 2.32 |

The results demonstrate that comparable results are obtained using the reformatted DVV protocol and the old DVVtest® and DVVconfirm® protocols on normal plasma and plasma with known LA.

Example 3

Comparison of Reformatted and Unformatted aPPT Screening Methods

The high phospholipid substrate was also tested for its ability to confirm a positive result using aPTT activator. The activator used in this study was from the STACLOT® LA kit by Diagnostica Stago (Asnieres, France). In this experiment, normal plasma and plasma known to contain LA were tested using the STACLOT® LA protocol of the manufacturer. The reformatted protocol was performed by substituting Reagent 1 with LA Buffer from the Acticlot dPT kit, and Reagent 2 with the high phospholipid substrate. All other reagents and procedures were performed according to the manufacturer's instructions.

The results in Table 3 show that the high phospholipid substrate was able to correct (confirm) the abnormal clot time of the LA sample to the same degree as the hexagonal phase phospholipid in the original kit. As expected, the high phospholipid substrate did not affect normal plasma. This shows that the phospholipid substrate described herein which confirms RVV and dPT activator induced clotting times of LA plasma also confirms LA identified with an aPTT activator. This would allow three LA screening tests to be performed and any or all three confirmed using a single reagent.

Table 3 shows confirmation of positive aPTT using high phospholipid substrate (PL), and includes a comparison to results obtained from using StaClot LA. Clotting times were determined in an ACL300 coagulation analyzer.

TABLE 3

| SAMPLE | Reformatted aPTT | | | StaClot LA Protocol (Diagnostica Stago) | | |
|---|---|---|---|---|---|---|
| | aPTT activator (sec) | +PL (sec) | T/C | StaClot (sec) | Hexagonal PL (sec) | T/C |
| PNP | 93.7 | 91.5 | 1.02 | 46.5 | 45.6 | 1.02 |
| LA | 142 | 80.5 | 1.76 | 95 | 53.7 | 1.77 |

Having thus described in detail preferred embodiments of the present invention, it is to be understood that the invention defined by the appended claims is not to be limited by particular details set forth in the above description as many apparent variations thereof are possible without departing from the spirit or scope.

We claim:
1. A kit for detecting antiphospholipid antibodies in a test plasma sample, comprising:
 (a) at least one negative control plasma sample;
 (b) at least one procoagulant test reagent suitable for activating the extrinsic coagulation pathway; and
 (c) a high phospholipid confirmatory substrate, wherein the high phospholipid confirmatory substrate is synthetic and is suitable for use as a confirmatory substrate with the at least one negative control plasma sample in (a) and in a coagulation assay involving the at least one procoagulant test reagent of (b),
 wherein the high phospholipid confirmatory substrate is at least 1 mg/ml phospholipid concentration and is used with at least two coagulation assays.

2. The kit of claim 1, wherein at least one coagulation assay is a dilute Russell Viper Venom Time assay (dRVVT), a dilute prothrombin time assay (dPT), or an activated partial thromboplastin time assay (aPTT), and wherein each assay comprises a screening step and a confirmatory step, wherein the confirmatory step of each assay uses the high phospholipid substrate of (c).

3. The kit of claim 1, wherein the antiphospholipid antibodies are selected from the group consisting of lupus anticoagulants, anti-β2-GP1 antibodies, anti-protein C antibodies, anti-protein S antibodies, anti-complement antibodies, anticardiolipin antibodies, anti-thrombin antibodies, anti-prothrombin antibodies, anti-thrombomodulin antibodies, anti-tPA antibodies, anti-Factor XII antibodies, anti-kininogen antibodies, anti-annexin V antibodies and combinations thereof.

4. The kit of claim 1, wherein the test plasma sample is derived from a subject at risk for or suffering from an autoimmune disorder.

5. The kit of claim 4, wherein the autoimmune disorder is selected from the group consisting of antiphospholipid syndrome (APS), connective tissue diseases, immune thrombocytopenia purpura, Hashimoto's thyroiditis, rheumatoid arthritis, and systemic lupus erythromatosus (SLE).

6. The kit of claim 1, further comprising a positive control plasma sample.

7. The kit of claim 1, wherein the at least one procoagulant test reagent is tissue factor.

8. The kit of claim 7, wherein the at least one procoagulant test reagent contains a low level of phospholipids.

9. The kit of claim 1, wherein the high phospholipid substrate comprises a component selected from the group consisting of phosphatidylserine (PS), phosphatidylcholine (PC), phosphatidylethanolamine (PE), phosphatidylinositol (PI), cardiolipin, phosphatidic acid, dioleoyl phosphatidylethanolamine (DOPE), phospholipid coated beads, phospholipid suspensions, and combinations thereof.

10. The kit of claim 1, further comprising a buffer containing calcium.

* * * * *